United States Patent
Jackson et al.

(10) Patent No.: US 10,842,809 B2
(45) Date of Patent: Nov. 24, 2020

(54) PET FOOD COMPOSITIONS

(71) Applicant: Hill's Pet Nutrition, Inc., Topeka, KS (US)

(72) Inventors: Matthew Jackson, Topeka, KS (US); Dennis Jewell, Lawrence, KS (US)

(73) Assignee: Hills Pet Nutrition, Inc., Topeka, KS (US)

( * ) Notice: Subject to any disclaimer, the term of this patent is extended or adjusted under 35 U.S.C. 154(b) by 414 days.

(21) Appl. No.: 15/381,783

(22) Filed: Dec. 16, 2016

(65) Prior Publication Data

US 2018/0169133 A1  Jun. 21, 2018

(51) Int. Cl.

| | |
|---|---|
| A61K 36/48 | (2006.01) |
| A61K 31/716 | (2006.01) |
| A23K 20/10 | (2016.01) |
| A61K 31/202 | (2006.01) |
| A23K 10/30 | (2016.01) |
| A23K 20/158 | (2016.01) |
| A23K 20/111 | (2016.01) |
| A61K 31/352 | (2006.01) |
| A61K 36/06 | (2006.01) |

(52) U.S. Cl.
CPC ............ *A61K 31/716* (2013.01); *A23K 10/30* (2016.05); *A23K 20/10* (2016.05); *A23K 20/111* (2016.05); *A23K 20/158* (2016.05); *A61K 31/202* (2013.01); *A61K 31/352* (2013.01); *A61K 36/06* (2013.01); *A61K 36/48* (2013.01)

(58) Field of Classification Search
None
See application file for complete search history.

(56) References Cited

U.S. PATENT DOCUMENTS

| | | |
|---|---|---|
| 6,458,378 B1 | 10/2002 | Sunvold |
| 6,936,598 B2 | 8/2005 | Khoo et al. |
| 8,226,973 B2 | 7/2012 | Pan |
| 8,753,668 B2 | 6/2014 | Sedmak |
| 9,427,002 B2 | 8/2016 | Pan |
| 2008/0187611 A1* | 8/2008 | Su .................. A61K 36/605 424/774 |

FOREIGN PATENT DOCUMENTS

| | | | |
|---|---|---|---|
| CN | 104366558 A | * | 2/2015 |
| CN | 104544095 A | * | 4/2015 |
| EP | 2364098 B1 | | 10/2016 |
| JP | 2002345411 A | * | 12/2002 |
| JP | 2007314492 A | * | 12/2007 |
| KR | 100439147 B1 | | 8/2002 |
| WO | 1990/004334 | | 5/1990 |
| WO | 2001/074345 | | 10/2001 |
| WO | 2001/078534 | | 10/2001 |
| WO | 2005/089567 | | 9/2005 |
| WO | WO2010149815 A1 | * | 12/2010 |
| WO | WO 2011/091111 | | 7/2011 |

OTHER PUBLICATIONS

De Boever et al., 2000, "Fermentation by gut microbiota cultured in a simulator of the human intestinal microbial ecosystem is improved by supplementing a soygerm powder," The Journal of Nutrition 130(10):2599-2606.

International Search Report and Written Opinion of the International Searching Authority in International Application No. PCT/US2017/063820, dated Mar. 9, 2018.

* cited by examiner

*Primary Examiner* — Ralph J Gitomer

(57) ABSTRACT

Described herein are pet food compositions comprising a blood glucose management component comprising soy isoflavone and yeast beta-glucan (β-glucan); along with methods of making and using same.

16 Claims, No Drawings

PET FOOD COMPOSITIONS

BACKGROUND

Pets require a healthy diet and proper digestion for continued growth and ordinary wellbeing. Oral consumption of yeast beta glucan (BG) is practiced for its benefits to the immune system. However, it is not generally recognized as a prebiotic fiber; and its use in place of more typical prebiotic fibers (e.g. hemicellulose and pectin rich beet and citrus pulps) has traditionally been associated with suboptimal colonic fermentation and acidification by commensal bacteria. Acidification of the colonic lumen by commensal bacteria is a critical to establishing a healthy microbiome and maintaining intestinal health Reversing the depressive effect of BG (relative to e.g. citrus and beet pulps) on colonic fermentation and acidification has been a challenge. Embodiments of the present invention are designed to meet these needs.

BRIEF SUMMARY

In some embodiments, the present invention provides a pet food composition comprising a blood glucose management component comprising soy isoflavone (SI) and BG.

In some embodiments, the present invention provides methods of controlling post-prandial glucose levels in in a companion animal comprising the step of feeding the companion animal a pet food composition comprising an effective amount of a blood glucose management component comprising SI and yeast BG.

In some embodiments, the present invention provides methods of inducing satiety in a companion animal comprising the step of feeding the companion animal a pet food composition comprising an effective amount of a blood glucose management component comprising SI and BG.

DETAILED DESCRIPTION

As used herein, "satiety" refers to satisfaction of the need for nutrition and the extinguishment of the sensation of hunger, which is often described as "feeling full". The satiety response refers to behavioral characteristics observed to be consistent with having consumed a sufficient amount of food, such as an abrupt or a tapered down cessation of eating. However, the biological mechanisms which lead to the satiety response are often triggered in a gradual or delayed manner, such that they are usually out of phase with the amount of food taken in by the animal prior to cessation, which results in the animal consuming more nutritional content than is appropriate for the animal. Satiety inducing agents produce an accelerated onset of the satiety response, i.e., pet food compositions containing satiety inducing agents will trigger the satiety response at an earlier point in time than would a similar pet food composition without the satiety inducing agent.

In the context of the present disclosure, the terms "yeast beta glucan", "β-glucan" and "BG" may be used interchangeably.

In the context of the present disclosure, the terms "soy isoflavone", "soy isolate" and "SI" may also be used interchangeably.

In some embodiments, the present invention provides a pet food composition comprising a blood glucose management component comprising SI and BG.

In some embodiments, the blood glucose management component is present in an amount effective to produce, after about 24 hours post-ingestion by a mammal, a short chain fatty acid (SCFA) complex having a propionate content greater than about 20% of the total SCFA produced. In other embodiments, the present invention provides a pet food composition wherein the blood glucose management component is present in an amount effective to produce, after about 24 hours post-ingestion by a mammal, a short chain fatty acid (SCFA) complex having a propionate content of greater than about 25% of the total SCFA produced. Still further embodiments provide a pet food composition wherein the blood glucose management component is present in an amount effective to produce, after about 24 hours post-ingestion by a mammal, a short chain fatty acid (SCFA) complex having a propionate content of about 30% of the total SCFA produced.

Further embodiments provide a pet food composition wherein the ratio of BG to SI (BG:SI) is from about 23:1 to about 7:1.

Still further embodiments provide a pet food composition wherein the blood glucose management component is present in an amount effective to produce, after about 6 hours post-ingestion by a mammal, a short chain fatty acid (SCFA) complex having a propionate content of about 20% of the total SCFA produced.

Other embodiments provide a pet food composition wherein the blood glucose management component is present in an amount effective to produce, after about 6 hours post-ingestion by a mammal, a short chain fatty acid (SCFA) complex having a propionate content of greater than about 20% of the total SCFA produced.

In some embodiments, the propionate content is greater after about 24 hours post-ingestion than the propionate content after about 6 hours post-ingestion.

Yet other embodiments provide a method of controlling post-prandial glucose levels in in a companion animal comprising the step of feeding the companion animal a pet food composition comprising an effective amount of a blood glucose management component comprising SI and BG. Some embodiments provide a method of controlling post-prandial glucose levels in a companion animal comprising the step of feeding the companion animal a pet food composition consisting essentially of an effective amount of a blood glucose management component comprising SI and BG.

The pet food compositions set forth herein may be formed by extrusion to form a kibble-type pet food composition. In some embodiments, the milled raw ingredients of the composition are extruded and then a surface coating comprising a palatant and/or a nutritional oil is applied. In some embodiments, the kibble is spray coated in a tumbling mixer with a composition comprising a palatant and/or a nutritional oil. In other embodiments, the kibble is coated using a vacuum enrobing technique, wherein the kibble is subjected to vacuum and then exposed to coating materials after which the release of the vacuum drives the coating materials inside the kibble.

The pet food compositions described herein can include any additional ingredients which provide adequate nutrition for the animal. For example, a typical canine or feline diet for use in the present invention may contain from about 17 to about 50% crude protein (and preferably about 20 to about 40%), from about 8 to about 40% fat (and preferably about 12 to about 22%), and from about 0.5 to about 20% total dietary fiber (and preferably about 2 to about 10%), along with the multiple starch source, all percentages by weight. However, no specific ratios or percentages of these nutrients are required.

In some embodiments, the compositions described herein comprise from about 17% to about 50% crude protein, by weight. The crude protein material may comprise vegetable proteins such as soybean meal, soy protein concentrate, corn gluten meal, wheat gluten, cottonseed, and peanut meal, or animal proteins such as casein, albumin, and meat protein. Examples of meat protein useful herein include beef, pork, lamb, equine, poultry, fish, and mixtures thereof.

In some embodiments, the compositions described herein comprise from about 8% to about 40% fat, by weight. Examples of suitable fats include animal fats and vegetable fats. Preferably the fat source is an animal fat source such as tallow or grease. Vegetable oils such as corn oil, sunflower oil, safflower oil, rape seed oil, soy bean oil, olive oil and other oils rich in monounsaturated and polyunsaturated fatty acids, may also be used.

In some embodiments, the compositions described herein comprise from about 10% to about 50% carbohydrate, by weight. Examples of suitable carbohydrates include grains or cereals such as rice, corn, millet, sorghum, alfalfa, barley, soybeans, canola, oats, wheat, rye, triticale and mixtures thereof. The compositions may also optionally comprise other materials such as dried whey and other dairy by-products.

In some embodiments, the compositions described herein comprise a fermentable fiber. In some embodiments, the fermentable fiber may be any fiber source which intestinal bacteria present in the animal can ferment to produce significant quantities of SCFAs. In some embodiments, the fermentable fiber is selected from beet pulp, gum arabic (including gum talha), psyllium, rice bran, carob bean gum, citrus pulp, pectin, fructooligosaccharides and inulin, mannanoligosaccharides and mixtures of these fibers.

The moisture content for the pet food compositions described herein can vary depending on the nature of the food composition. In some embodiments, the pet food compositions may be dry compositions (e.g., kibble), semi-moist compositions, wet compositions, or any mixture thereof. In some embodiments, the pet food composition is a complete and nutritionally balanced pet food. In some embodiments, the pet food may be a "wet food", "dry food", or food of "intermediate moisture" content.

As used herein, "wet food" describes a pet food that is typically sold in cans or foil bags and has a moisture content typically in the range of about 70% to about 90%, by weight.

As used herein, "dry food" describes a pet food that is of a similar composition to wet food but contains a limited moisture content typically in the range of about 5% to about 15% or 20%, by weight (typically in the form or small biscuit-like kibbles). In one embodiment, the compositions have moisture content from about 5% to about 20%, by weight. Dry food products include a variety of foods of various moisture contents, such that they are relatively shelf-stable and resistant to microbial or fungal deterioration or contamination. In some embodiments, dry food compositions are extruded food products such as pet foods or snack foods for companion animals.

In some embodiments, the pet food compositions described herein may also comprise one or more fiber sources. As used herein, the term "fiber" includes all sources of "bulk" in the pet food composition whether digestible or indigestible, soluble or insoluble, fermentable or nonfermentable. In some embodiments, the fiber comprises a fiber from a plant source such as marine plants, but microbial sources of fiber may also be used. A variety of soluble or insoluble fibers may be utilized, as will be known to those of ordinary skill in the art. The fiber source can be beet pulp (from sugar beet), gum arabic, gum talha, psyllium, rice bran, carob bean gum, citrus pulp, pectin, fructooligosaccharide, short chain oligofructose, mannanoligofructose, soy fiber, arabinogalactan, galactooligosaccharide, arabinoxylan, or mixtures thereof.

Alternatively, the fiber source can be a fermentable fiber. Fermentable fiber has previously been described to provide a benefit to the immune system of a companion animal. Fermentable fiber or other compositions known to skilled artisans that provide a prebiotic to enhance the growth of probiotics within the intestine may also be incorporated into the composition to aid in the enhancement of the benefit provided by the invention to the immune system of an animal.

In some embodiments, the ash content of the pet food composition ranges from less than 1% to about 15%, by weight, preferably from about 5% to about 10%, by weight.

In some embodiments, the pet food composition comprises from about 17% to about 50% protein, from about 8% to about 40% fat, from about 5% to about 10% ash content, and has a moisture content of about 5% to about 20%, by weight. In other embodiments, the pet food composition further comprises probiotics or prebiotics as described herein.

In some embodiments, the compositions described herein can be used as a dietary supplement and be co-administered with another pet food composition. The dietary supplement can have any suitable form such as a gravy, drinking water, beverage, yogurt, powder, granule, paste, suspension, chew, morsel, treat, snack, pellet, pill, capsule, tablet, sachet, or any other suitable delivery form. The dietary supplement can comprise the dietary formulations and optional compounds such as vitamins, preservatives, probiotics, prebiotics, and antioxidants. This permits the supplement to be administered to the animal in small amounts, or in the alternative, can be diluted before administration. In some embodiments, the dietary supplement may be admixed with a pet food composition or with water or other diluent prior to administration to the animal. When administered in a dietary supplement, the dietary formulations comprise from about 0.1 to about 90% of the supplement, preferably from about 3 to about 70%, more preferably from about 5 to about 60%, by weight.

In some embodiments, the compositions described herein are administered to an animal in the form of a nutraceutical composition. The nutraceutical composition comprises any-one of the pet food compositions described herein and one or more nutraceutically acceptable carriers, diluents, or excipients. Generally, nutraceutical compositions are prepared by admixing a compound or composition with excipients, buffers, binders, plasticizers, colorants, diluents, compressing agents, lubricants, flavorants, moistening agents, and the like, including other ingredients known to skilled artisans to be useful for producing nutraceuticals and formulating compositions that are suitable for administration to an animal as a nutraceutical. When administered in a nutraceutical composition, the dietary formulations comprise from about 0.1 to about 90% of the composition, preferably from about 3 to about 70%, more preferably from about 5 to about 60%, by weight.

The compositions described herein can be administered to the animal on an as-needed, on an as-desired basis, or on a regular basis. A goal of administration on a regular basis is to provide the animal with a regular and consistent amount of SI and BG or the direct or indirect metabolites that result from such ingestion.

According to the methods of the invention, administration of the dietary formulations, including administration as part of a dietary regimen, can span a period ranging from parturition through the adult life of the animal. In various embodiments, the animal is a companion animal such as a dog or cat. In certain embodiments, the animal is a young or growing animal. In some embodiments, the animal is an aging animal. In other embodiments administration begins, for example, on a regular or extended regular basis, when the animal has reached more than about 30%, 40%, or 50% of its projected or anticipated lifespan. In some embodiments, the animal has attained 40, 45, or 50% of its anticipated lifespan. In yet other embodiments, the animal is older having reached 60, 66, 70, 75, or 80% of its likely lifespan. A determination of lifespan may be based on actuarial tables, calculations, estimates, or the like, and may consider past, present, and future influences or factors that are known to positively or negatively affect lifespan. Consideration of species, gender, size, genetic factors, environmental factors and stressors, present and past health status, past and present nutritional status, stressors, and the like may also influence or be taken into consideration when determining lifespan.

The compositions described herein are administered to an animal for a time required to accomplish one or more objectives of the invention, e.g., managing or controlling blood glucose; preventing or treating insulin resistance; improving insulin sensitivity; extending the prime; improving the quality of life; and promoting the health and wellness in an animal. In some embodiments, the compositions described herein are administered to an animal on a regular basis.

In various embodiments, the compositions comprising the dietary formulations contain at least one of (1) one or more probiotics; (2) one or more inactivated probiotics; (3) one or more components of inactivated probiotics that promote health benefits similar to or the same as the probiotics, e.g., proteins, lipids, glycoproteins, and the like; (4) one or more prebiotics; and (5) combinations thereof. The probiotics or their components can be integrated into the compositions comprising the dietary formulations (e.g., uniformly or non-uniformly distributed in the compositions) or applied to the compositions comprising the dietary formulations (e.g., topically applied with or without a carrier). Such methods are known to skilled artisans, e.g., U.S. Pat. No. 5,968,569 and related patents.

Typical probiotics include, but are not limited to, probiotic strains selected from *Lactobacilli*, *Bifidobacteria*, or *Enterococci*, e.g., *Lactobacillus reuteri*, *Lactobacillus acidophilus*, *Lactobacillus animalis*, *Lactobacillus ruminis*, *Lactobacillus johnsonii*, *Lactobacillus casei*, *Lactobacillus paracasei*, *Lactobacillus rhamnosus*, *Lactobacillus fermentum*, and *Bifidobacterium* sp., *Enterococcus faecium* and *Enterococcus* sp. In some embodiments, the probiotic strain is selected from the group consisting of *Lactobacillus reuteri* (NCC2581; CNCM 1-2448), *Lactobacillus reuteri* (NCC2592; CNCM 1-2450), *Lactobacillus rhamnosus* (NCC2583; CNCM 1-2449), *Lactobacillus reuteri* (NCC2603; CNCM 1-2451), *Lactobacillus reuteri* (NCC2613; CNCM 1-2452), *Lactobacillus acidophilus* (NCC2628; CNCM 1-2453), *Bifidobacterium adolescentis* (e.g., NCC2627), *Bificlobacterium* sp. NCC2657 or *Enterococcus faecium* SF68 (NCIMB 10415).

In some embodiments, the compositions described herein may contain one or more prebiotics, e.g., fructo-oligosaccharides, gluco-oligosaccharides, galacto-oligosaccharides, isomalto-oligosaccharides, xylo-oligosaccharides, soybean oligosaccharides, lactosucrose, lactulose, and isornaltulose.

In one embodiment, the prebiotic is chicory root, chicory root extract, insulin, or combinations thereof. Generally, prebiotics are administered in amounts sufficient to positively stimulate the healthy microflora in the gut and cause these "good" bacteria to reproduce.

The probiotics and prebiotics can be made part of the composition by any suitable means. Generally, the agents are mixed with the composition or applied to the surface of the composition, e.g., by sprinkling or spraying. In some embodiments, the pet food composition contains from about 0.1 to about 10% prebiotic, by weight. The prebiotics can be integrated into the compositions using methods known to skilled artisans.

In some embodiments, the prebiotic fiber component comprises beet pulp, citrus pulp, a cellulosic material or a mixture thereof. In other embodiments, the prebiotic fiber component comprises a mixture of beet pulp and citrus pulp.

In some embodiments, the total fiber content of the pet food composition is about 0.01%, by weight. In some embodiments, the SI is present at concentration of from about 0.005% to about 0.10%, by weight. In some embodiments, the SI is present at concentration of from about 0.01% to about 0.05%, by weight. In some embodiments, the SI is present at concentration of from about 0.02% to about 0.04%, by weight. In some embodiments, the SI is present at about 0.03%, by weight. In some embodiments, the SI is of the type available from Naturex of South Hackensack, N.J.

In some embodiments, the BG is present at concentration of from about 0.01% to about 1%, by weight. In some embodiments, the BG is present at concentration of from about 0.05% to about 0.75%, by weight. In some embodiments, the BG is present at concentration of from about 0.25% to about 0.6%, by weight. In some embodiments, the BG is present at about 0.40%, by weight. In some embodiments, the BG is of the type available from Sensient Flavors, LLC of Indianapolis, Ind.

In some embodiments, the pet food compositions further comprise from about 17% to about 50% protein. In other embodiments, the pet food compositions of the present invention comprise a source of hydrolyzed animal or plant protein. In some embodiments, the source of hydrolyzed animal or plant protein comprises chicken liver. In further embodiments, the source of hydrolyzed animal or plant protein is present in an active content of from about 25 to about 45%, by weight.

Further embodiments of the present invention provide methods of inducing satiety in a companion animal comprising the step of feeding the companion animal a pet food composition comprising an effective amount of a blood glucose management component comprising SI and BG. While other embodiments of the present invention provide methods of inducing satiety in a companion animal comprising the step of feeding the companion animal a pet food composition consisting essentially of an effective amount of a blood glucose management component comprising soy isoflavone and yeast beta-glucan (β-glucan).

The invention will now be described in conjunction with the following, non-limiting examples.

EXAMPLES

Example 1

An exemplary pet food composition (Example 1) is prepared as set forth in Table 1 below. All amounts are provided in weight percent, based upon total weight of the pet food composition. The composition is formulated according to the nutrition standards set forth by the American Associated of Feed Control Officials (AAFCO) and the National Research Council (NRC). The composition may be produced by extrusion, dried, and then optionally coated with palatants.

teria were incubated with prebiotic fiber as a carbon source as well as a published minimal media. During (6 hours) and after (24 hours) of anaerobic incubation, production of SCFA, including acetate, propionate and butyrate were measured. The results of this experiment are described in Table 2 (below).

TABLE 2

| Ingredient | Ex. 1 | Ex. 2 | Ex. 3 | Comp. Ex. 1 | Comp. Ex. 2 | Comp. Ex. 3 | Comp. Ex. 4 | Comp. Ex. 5 |
|---|---|---|---|---|---|---|---|---|
| | % w/v | | | | | | | |
| Beet Pulp | 0.00286 | 0.00429 | 0.00571 | 0.00286 | 0.00429 | 0.00571 | 0.00714 | 0.00714 |
| Citrus Pulp | 0.005 | 0.0075 | 0.01 | 0.005 | 0.0075 | 0.01 | 0.0125 | 0.0125 |
| Soy Isoflavone | 0.00025 | 0.00025 | 0.00025 | — | — | — | — | 0.00025 |
| Yeast β-Glucan | 0.00857 | 0.00571 | 0.00286 | 0.00857 | 0.00571 | 0.00286 | — | — |
| Total Fiber | 0.01 | 0.01 | 0.01 | 0.01 | 0.01 | 0.01 | 0.01 | 0.01 |
| | Propionate: Total SCFA (%) | | | | | | | |
| 6 hours ($t_6$) | 22.39 | 22.11 | 19.88 | 16.29 | 16.43 | 15.07 | 14.38 | 17.18 |
| 24 hours ($t_{24}$) | 29.66 | 25.26 | 20.78 | 13.89 | 11.54 | 10.66 | 10.18 | 18.31 |

TABLE 1

| Ingredient | Preferred Active Content Range (wt %) |
|---|---|
| SI | 0.01-0.05 |
| BG | 0.1-1 |
| Corn, starch, common canning | 40-50 |
| Hydrolyzed Chicken Liver and Heart | 30-35 |
| Soybean oil, crude, degummed | 1-5 |
| Cellulose, Pelleted | 1-5 |
| Chicken, liver, digest, optimizor LDPE H | 1-3 |
| Lactic acid, food grade | 1-2 |
| Calcium carbonate | 1-2 |
| Dicalcium phosphate | 1-2 |
| Choice White Grease/Phos Acid | 0.1-2 |
| Flav Gen#1 + CWG | 0.1-1 |
| Glyceryl monostearate | 0.1-1 |
| Potassium chloride | 0.1-1 |
| Natural flavor, Pork, Liver, Digest, D'T | 0.1-1 |
| Sodium chloride, iodized | 0.1-1 |
| Choline chloride, liquid, 70% | 0.1-1 |

Example 2

Five (5) canines were randomly selected from a general population of beagles and mixed breed dogs. The canine subjects consisted of both neutered males and spayed females, who consumed varied, but typical, canine maintenance foods. The canines were selected to provide a varied compilation of feces that accurately represents the companion animal canine population at large; and would allow an objective assessment of the impact that a specific ingredient, or combination thereof, may have on a particular endpoint.

Example 3

Feces were collected from dogs fasted overnight into plastic bags containing oxygen absorbing packs to reduce oxygen tension and maintain viability of anaerobic microbiota. Pooled feces were homogenized in bacterial minimal media and separated of the largest particulates by centrifugation. After adding glycerol as a cryoprotectant the aliquot of viable bacteria were frozen and stored at (−) 80° C. Soy Isoflavone and prebiotic fiber blends were sterilized via pasteurization prior to reconstitution in sterile water. Bacteria were incubated with prebiotic fiber as a carbon source as well as a published minimal media. During (6 hours) and after (24 hours) of anaerobic incubation, production of SCFA, including acetate, propionate and butyrate were measured. The results of this experiment are described in Table 2 (below).

As illustrated by the data reported in Table 2 (above), increasing BG and reducing typical prebiotics (e.g. beet pulp and citrus pulp) decreased SCFA production. However, the addition of soy isoflavone unexpectedly increased production of SCFA after both 6 hour and 24 hour incubation periods. It follows, therefore, that the combination of soy isoflavone and BG shifted the type of SCFA produced to favor propionate at the expense of other SCFA after both 6 hour and 24 hour incubation periods. Propionate is gluconeogenic precursor and enterohepatically recirculated, microbially derived propionate can serve to normalize postprandial glucose shifts and increase satiety. As such, these results demonstrate that exemplary compositions of the present invention are effective in normalizing post-prandial glucose shifts and increasing satiety, which correlates with an overall improvement in blood glucose management.

Without being bound by theory, it is believed that SE is not serving as a fermentable carbon source, as its inclusion rate is low. Rather, it appears that SE unexpectedly shifts the microbiome composition or substrate preference.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A pet food composition comprising a blood glucose management component comprising soy isoflavone and yeast beta-glucan (β-glucan), wherein the blood glucose management component is present in an amount effective to produce, after about 24 hours post-ingestion by a mammal, a short chain fatty acid (SCFA) complex having a propionate content greater than about 20% of the total SCFA produced, and wherein the ratio of yeast beta glucan to soy isoflavone (yeast beta glucan:soy isoflavone) is from about 23:1 to about 7:1 by weight.

2. The pet food composition according to claim 1, wherein the blood glucose management component is present in an amount effective to produce, after about 24 hours post-ingestion by a mammal, a short chain fatty acid (SCFA) complex having a propionate content of about 30% of the total SCFA produced.

3. The pet food composition according to claim 1, wherein the blood glucose management component is present in an amount effective to produce, after about 6 hours post-ingestion by a mammal, a short chain fatty acid (SCFA) complex having a propionate content of about 20% of the total SCFA produced.

4. The pet food composition according to claim 1, further comprising a prebiotic fiber component.

5. The pet food composition according to claim 4, wherein the prebiotic fiber component comprises beet pulp, citrus pulp, a cellulosic material or a mixture thereof.

6. The pet food composition according to claim 5, wherein the prebiotic fiber component comprises a mixture of beet pulp and citrus pulp.

7. The pet food composition according to claim 1, wherein the total fiber concentration is about 0.01%, by weight.

8. The pet food composition according to claim 1, wherein the soy isoflavone is present at about 0.03%, by weight.

9. The pet food composition according to claim 1, wherein the β-glucan is present at about 0.40%, by weight.

10. The pet food composition according to claim 1, further comprising from about 17% to about 50% protein, by weight.

11. The pet food composition according to claim 1, further comprising a source of hydrolyzed animal or plant protein.

12. The pet food composition according to claim 11, wherein the source of hydrolyzed animal or plant protein comprises chicken liver.

13. The pet food composition according to claim 11, wherein the source of hydrolyzed animal or plant protein is present in an active content of from about 25 to about 45%, by weight.

14. The pet food composition according to claim 1, having an ash content of from about 5% to about 10%, by weight.

15. The pet food composition according to claim 1, having a moisture content of from about 5% to about 20%, by weight.

16. The pet food composition according to claim 1, further comprising high docosahexaenoate fish oil.

* * * * *